United States Patent [19]

Roduit

[11] Patent Number: 5,364,939
[45] Date of Patent: Nov. 15, 1994

[54] PROCESS FOR THE PRODUCTION OF CARBOXYLIC ACID CHLORIDES OF AROMATIC NITROGEN HETEROCYCLES

[76] Inventor: Jean-Paul Roduit, 4 Bois-de-Finges, Sierre, Switzerland

[21] Appl. No.: 32,328

[22] Filed: Mar. 17, 1993

[30] Foreign Application Priority Data

Mar. 20, 1992 [CH] Switzerland .................. 899/92

[51] Int. Cl.$^5$ .................. C07D 241/24; C07D 213/54; C07D 213/55; C07D 213/61
[52] U.S. Cl. .................. 544/406; 546/298; 546/314; 546/315
[58] Field of Search ............ 546/345, 314, 315, 298; 544/406

[56] References Cited

U.S. PATENT DOCUMENTS

| | | | |
|---|---|---|---|
| 4,081,451 | 3/1978 | Mayer | 546/318 |
| 4,144,238 | 3/1979 | Said | 546/318 |

FOREIGN PATENT DOCUMENTS

| | | | |
|---|---|---|---|
| 032516 | 7/1981 | European Pat. Off. | 546/340 |
| 2713316 | 10/1977 | Germany | 546/318 |
| 2001318A | 1/1979 | United Kingdom | 562/840 |

OTHER PUBLICATIONS

Fischer et al., BPR, D., Chem. ges., 45, (1912), pp. 2456–2467.
Ber. D. Chem. ges., 45, (1912), p. 2461.

Primary Examiner—Alan L. Rotman

[57] ABSTRACT

The process for the production of the carboxylic acid chlorides of the aromatic nitrogen heterocycles of the series of the compounds of the general formulas:

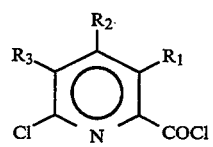

I

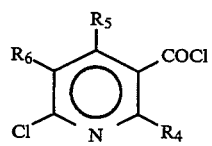

II

-continued

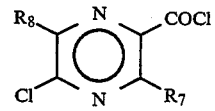

III

The hydroxy carboxylic acids of the aromatic nitrogen heterocycles from the series of the compounds of the general formulas:

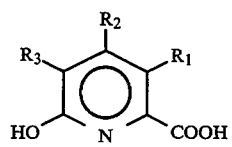

IV

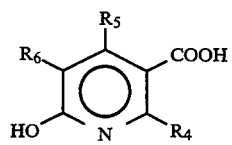

V

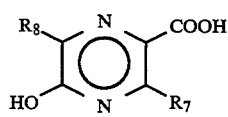

VI

In the general formulas I to VI, $R_1$, $R_2$, $R_3$, $R_4$, $R_5$, $R_6$, $R_7$ and $R_8$ are the same or different and each is a hydrogen atom or a halogen atom. The chlorination is performed with a solution of phosphorous pentachloride in phosphoroxy chloride. The excess phosphorous pentachloride is converted into phosphoroxy chloride either with a $C_1$–$C_4$-carboxylic acid or with a silane of the general formula:

$(CH_3)_3—Si—OR_9$   VII

Then the product according to one of the general formulas I to III is isolated.

11 Claims, No Drawings

PROCESS FOR THE PRODUCTION OF CARBOXYLIC ACID CHLORIDES OF AROMATIC NITROGEN HETEROCYCLES

BACKGROUND OF THE INVENTION

1. Field Of The Invention

The invention relates to a new process for the production of carboxylic acid chlorides of aromatic nitrogen heterocycles of the series of compounds of general formulas:

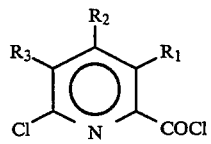   I

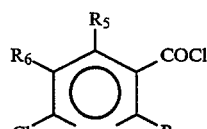   II

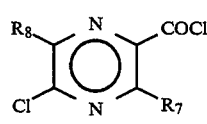   III by chlorination of the corresponding hydroxy carboxylic acids of aromatic nitrogen heterocycles from the series of compounds of the general formulas:

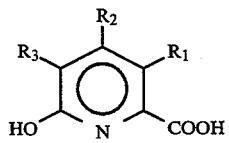   IV

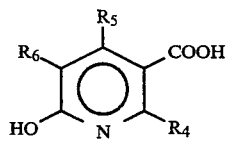   V

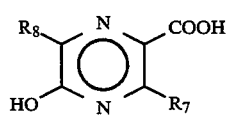   VI

In the above general formulas I to VI, $R_1$, $R_2$, $R_3$, $R_4$, $R_5$, $R_6$, $R_7$ and $R_8$ are the same or different and each is a hydrogen atom or a halogen atom.

These carboxylic acid chlorides of aromatic nitrogen heterocycles, such as, 6-chloropicolinic acid chloride, are important intermediate products for the production of herbicides [European Published Patent Application No. 447,004].

2. Background Art

The direct reaction of 6-hydroxypicolinic acid to 6-chloropicolinic acid chloride has not yet been described in the literature. Only the chlorination of 6-hydroxypicolinic acid to 6-chloropicolinic acid with phosphorous pentachloride in phosphoroxy chloride is known [Ber. D. Chem. ges., 45, (1912), page 2461]. 6-Chloropicolinic acid chloride can then be produced only by another chlorination of 6-chloropicolinic acid with, for example, thionyl chloride. A drawback of this process is the fact that under these conditions the product can only be produced by a 2-stage synthesis and that large amounts of phosphoric acid accumulate in the first stage as waste product in the working-up of 6-chloropicolinic acid as the intermediate product.

Also, the production of 6-chloropicolinic acid chloride, starting from 6-chloro-2-methylpyridine, is known [European Published Patent Application No. 032516]. A great drawback of this process is the fact that the feedstock 6-chloro-2 -methylpyridine must first be oxidized in a first stage with potassium permanganate to 6-chloropicolinic acid, the latter compound is then converted with thionyl chloride in the second stage into 6-chloropicolinic acid chloride, and the product is obtained in a moderate yield.

BROAD DESCRIPTION OF THE INVENTION

The main object of the invention is to provide a simple and economical process for the production of carboxylic acid chlorides of aromatic nitrogen heterocycles and where the products can be isolated in very good yields. Other objects and advantages of the invention are set out herein or are obvious herefrom to one skilled in the art.

The objects and advantages of the invention are achieved by the process and compounds of the invention.

The invention involves a process for the production of a carboxylic acid chloride of the aromatic nitrogen heterocycles of the series of the compounds of the general formula:

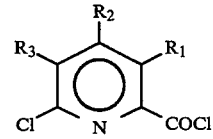   I

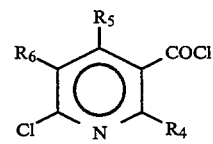   II

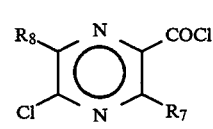   III wherein $R_1$, $R_2$, $R_3$, $R_4$, $R_5$, $R_6$, $R_7$ and $R_8$ are the same or different and each is a hydrogen atom or a halogen atom. A corresponding hydroxy carboxylic acid of the aromatic nitrogen heterocycles of the series of the compounds of the general formula:

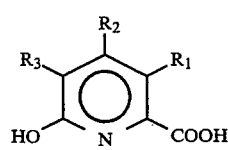   IV

-continued

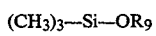
V

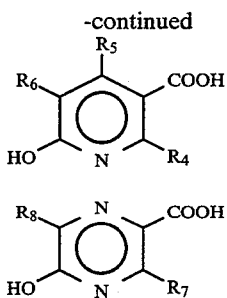

VI wherein $R_1$ to $R_8$ have the above-mentioned meanings, are chlorinated. The chlorination is performed with a solution of phosphorous pentachloride in phosphoroxy chloride. The excess phosphorous pentachloride is converted into phosphoroxy chloride either with a $C_1$–$C_4$-carboxylic acid or with a silane of the general formula:

$$(CH_3)_3\text{—Si—}OR_9 \qquad \text{VII}$$

wherein $R_9$ is a $C_1$–$C_4$-alkyl group or a tri($C_1$–$C_4$)alkylsilyl group. Then the product according to one of the general formulas I to III is isolated.

Preferably the $C_1$–$C_4$-carboxylic acid is formic acid. Preferably methoxytrimethyl silane, in which $R_9$ is a methyl group, or hexamethyl disiloxane, in which $R_9$ is a trimethyl group, is used as the silane of the general formula VII. Preferably the hydroxy carboxylic acid of the aromatic nitrogen heterocycles of the general formula IV is 6-hydroxypicolinic acid, wherein $R_1$, $R_2$ and $R_3$ each is a hydrogen atom, or 6-hydroxy-3,5-dichloropicolinic acid, wherein $R_2$ is a hydrogen atom, and $R_1$ and $R_3$ is a chloride atom, or the hydroxy carboxylic acid of the aromatic nitrogen heterocycles of the general formula VI is 5-hydroxypyrazine carboxylic acid, wherein $R_7$ and $R_8$ each is a hydrogen atom.

Preferably the chlorination is performed at a temperature of 20° to 110° C. Preferably the addition of the $C_1$–$C_4$-carboxylic acid or the silane of the general formula VII is performed at a temperature of 0° to 60° C. Preferably the phosphoroxy chloride is removed by distillation.

The invention also involves 3,5,6-trichloro-picolinic acid chloride, which is a compound of the general Formula I wherein $R_1$ and $R_3$ each is a chlorine atom and $R_2$ is a hydrogen atom.

DETAILED DESCRIPTION OF THE INVENTION

The invention process provides for the production of the carboxylic acid chlorides of the aromatic nitrogen heterocycles of the series of compounds of the general formulas:

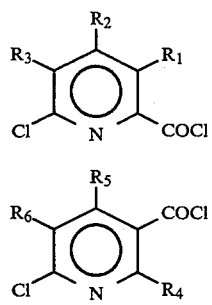
I

II

-continued

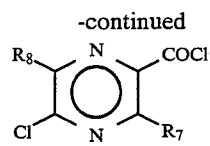
III wherein $R_1$, $R_2$, $R_3$, $R_4$, $R_5$, $R_6$, $R_7$ and $R_8$ are the same or different and each is a hydrogen atom or a halogen atom, respectively from the hydroxy carboxylic acids of the aromatic nitrogen heterocycles of the series of the compounds of the general formulas:

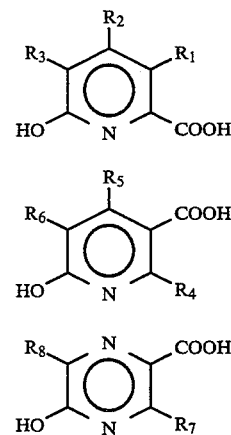
IV

V

VI wherein $R_1$ to $R_8$ have the mentioned meanings, A compound of one of the general formulas IV to VI is chlorinated. The chlorination is performed with a solution of phosphorous pentachloride in phosphoroxy chloride. The excess phosphorous pentachloride is converted into phosphoroxy chloride either with a $C_1$–$C_4$-carboxylic acid or with a silane of the general formula:

$$(CH_3)_3\text{—Si—}OR_9 \qquad \text{VII}$$

wherein $R_9$ is a $C_1$–$C_4$-alkyl group or a tri($C_1$–$C_4$)alkylsilyl group. Then the product according to one of the general formulas I to III is isolated.

A special advantage of the invention process is the fact that the carboxylic acid chlorides of aromatic nitrogen heterocycles can be isolated by the addition of easily available reagents, such as, formic acid.

The feedstocks, the aromatic hydroxy carboxylic acids of the nitrogen heterocycles, can be microbiologically produced in a simple way, for example, according to Swiss Patent Application No. 3572/91 or U.S. patent application Ser. No. 07/984,450, filed on Dec. 2, 1992. Details of said microbiological process for preparing the feedstock aromatic hydroxy carboxylic acids of the nitrogen heterocycles of the general formulas V and VI are set out below.

As feedstocks, the hydroxy carboxylic acids of the aromatic nitrogen heterocycles from the series of the compounds of the general formulas IV to VI are used.

Preferably 6-hydroxypicolinic acid, wherein $R_1$, $R_2$ and $R_3$ each is a hydrogen atom or 6-hydroxy-3,5-dichloropicolinic acid, wherein $R_2$ is a hydrogen atom and $R_1$ and $R_3$ is a chlorine atom, is used as the hydroxy carboxylic acid of the aromatic nitrogen heterocycles of the general formula IV. As the aromatic hydroxy carboxylic acid of the aromatic nitrogen heterocycles of the general formula VI preferably 5-hydroxypyrazine carboxylic acid, wherein $R_7$ and $R_8$ each is a hydrogen atom, is used.

The chlorination of the feedstocks with phosphorous pentachloride in phosphoroxy chloride usually takes place with an excess of the phosphorous pentachloride relative to the amount of the feedstock used. Suitably the phosphorous pentachloride is used in an amount of 1 to 3 mol, preferably from 2 to 2.5 mol, per mole of the feedstock (the hydroxy carboxylic acid of the aromatic nitrogen heterocycles). Suitably the chlorination is performed at a temperature of 20° to 110° C., preferably from 60° to 110° C.

After a usual chlorination time of 2 to 15 hours, suitably until no more HCl-gas is formed, according to the invention the excess phosphorous pentachloride is then converted either with a $C_1$–$C_4$-carboxylic acid or with a silane of the general formula VII into phosphoroxy chloride. Formic acid, acetic acid or propionic acid can be used, for example, as the $C_1$–$C_4$-carboxylic acids. Preferably formic acid is used as the $C_1$–$C_4$-carboxylic acid, with carbon monoxide and HCl are formed. As the silanes of the general formula:

$$(CH_3)_3-Si-OR_9 \quad \text{VII}$$

suitably methoxytrimethyl silane, wherein $R_9$ is a methyl group, or hexamethyl disiloxane, wherein $R_9$ is a trimethylsilyl group, is used. Suitably the $C_1$–$C_4$-carboxylic acid or the silane according to the general formula VII is used in an amount of 0.1 to 2 mol, preferably of 1 to 1.5 mol, per mole of the feedstock. The addition of the $C_1$–$C_4$-carboxylic acid or the silane of the general formula VII suitably takes place at a temperature of 0° to 60° C., preferably of 20° to 40° C.

During or after a usual addition time of 15 to 60 minutes, the thus-formed phosphoroxy chloride can be removed by distillation. Preferably the phosphoroxy chloride is removed by distillation and optionally is recycled into the reaction solution. In this way pure phosphoroxy chloride, which can be used again for the reaction, is produced in excess.

3,5,6-Trichloropicolinic acid chloride, which is a compound of the general formula I wherein $R_1$ and $R_3$ each is a chlorine atom and $R_2$ is a hydrogen atom, has not yet been described in the prior art and is part of the invention.

EXAMPLE 1

6-Chloropicolinic Acid Chloride 49.9 g (239.5 mmol) of phosphorous pentachloride was added at room temperature to a suspension of 6-hydroxypicolinic acid (71.9 mmol; 10 g) in phosphoroxy chloride (165.4 mmol; 25.3 g). An exothermic reaction was observed, and HCl-gas was formed. After completion of this exothermic reaction the mixture was heated within 1.5 hours to 90° C. Then this temperature was maintained for 12 hours. The clear solution was cooled to 30° C. Then formic acid (93.5 mmol; 4.3 g) was instilled, and HCl gas and CO gas was formed. After distilling-off of the phosphoroxy chloride, 6-chloropicolinic acid chloride was distilled at 90° C. at a pressure of 0.026 mbar. 12 g of 6-chloropicolinic acid chloride (68.2 mmol) was obtained as a white solid corresponding to a yield of 94.8 percent. The melting point of the product was 73.1° to 75.8° C. Other data concerning the product was:

$^1$H-NMR: (CDCl$_3$) (360 MHz) δ 7.66 (d, 9.6 Hz); 7.90 (t, 9.6 Hz); 8.07 (d, 9.6 Hz).

EXAMPLE 2

6-Chloropicolinic Acid Chloride

Analogously to Example 1, 100 g of 6-hydroxypicolinic acid was chlorinated to 6-chloropicolinic acid chloride, which resulted in a yield of 97.3 percent.

EXAMPLE 3

3,5,6-Trichloropicolinic Acid Chloride

Corresponding to Example 1, 10 g (48 mmol) of 3,5-dichloro-6-hydroxypicolinic acid was chlorinated with phosphorous pentachloride (158.6 mmol; 33.1 g) in phosphoroxy chloride (171 mmol; 26.3 g) at a temperature of 110° C. During the reaction 13 g of phosphoroxy chloride was already distilled by the addition of formic acid, as in Example 1. After the distillation, at 110° C. and 0.065 mbar, 7.8 g of 3,5,6-trichloropicolinic acid chloride corresponding to a yield of 66 percent was obtained. The melting point of the product was 49° to 52° C. Other data concerning the product was:

$^1$H-NMR: (CDCl$_3$) (360 MHz) 8.00 ppm; (s).

EXAMPLE 4

5-Chloropyrazine Carboxylic Acid Chloride

Corresponding to Example 1, 5-hydroxypyrazine-2-carboxylic acid (57.1 mmol; 8 g) was reacted with phosphorous pentachloride (188.4 mmol; 39.3 g) in phosphoroxy chloride (131.3 mmol, 20.15 g) at a temperature of 85° to 5-chloropyrazine-2-carboxylic acid chloride. After addition of formic acid, as in Example 1, and distillation at 85° C., 1.3 mbar, 6.7 g of 5-chloropyrazine-2-carboxylic acid chloride was obtained in the form of white crystals corresponding to a yield of 63 percent. The melting point of the product was >45° C. Other data concerning the product was:

$^1$H-NMR: (CDCl$_3$) (360 MHz) δ 8.78 (s); 9.10 (s).

EXAMPLE 5

6-Chloropicolinic Acid Chloride (a) Corresponding to Example 1, 6-hydroxypicolinic acid was chlorinated with phosphorous pentachloride in phosphoroxy chloride. After completion of the reaction, 10.5 g (100 mmol) of methoxytrimethylsilane was added at 50° C., and the formation of chloromethane was observed. After distilling-off of phosphoroxy chloride, 12.05 g of product was obtained corresponding to a yield of 95 percent.

(b) Corresponding to Example 5(a), 6-chloropicolinic acid chloride was produced with hexamethyldisiloxane (16.2 g) and 12.05 g of product was obtained corresponding to a yield of 95 percent.

The following deals with the above-mentioned microbiological process for the production of hydroxy-heterocyclic carboxylic acids of the general formula:

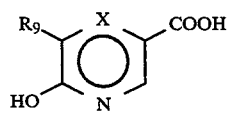

wherein $R_9$ is a hydrogen or a halogen atom and X is a nitrogen atom or a $CR_{10}$ function, wherein $R_{10}$ is a hydrogen or halogen atom. The aromatic hydroxy carboxylic acids of the nitrogen heterocycles of the general formulas V and VI are within the scope of the general formula VII. In the process, in step (a), an aerobic biomass which utilizes nicotinic acid or its soluble salts is cultivated with nicotinic acid or its soluble salts and a mineral acid in a molar ratio of nicotinic acid or its soluble salts to the mineral acid of 1 to 8. This ratio is assured over the entire cultivation phase. Then, in step (b), the hydroxylation of the corresponding heterocyclic carboxylic acid of the general formula:

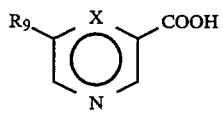   VIII wherein $R_9$ and X have the above-mentioned meanings, or its soluble salts, is performed with the biomass. Preferably, in step (a), sulfuric acid in a molar ratio of nicotinic acid or its soluble salts to sulfuric acid of 3 to 5 is used as the mineral acid. Preferably, in the cultivation phase in step (a), microorganisms of species *Pseudomonas acidovorans* DSM 7205, and/or species *Pseudomonas acidovorans* DSM 7203, and/or species *Alcaligenes faecalis* DSM 7204 and/or microorganisms with the designation DSM 7202 are concentrated and then, in step (b), the hydroxylation takes place with these microorganisms. Preferably, in step (b) as the heterocyclic carboxylic acid, nicotinic acid or its soluble salts is hydroxylated to 6-hydroxynicotinic acid. Preferably, in step (b) as the heterocyclic carboxylic acid, pyrazine carboxylic acid or its soluble salts is hydroxylated to 5-hydroxypyrazine carboxylic acid. Preferably the cultivation in step (a) and the hydroxylation in step (b) are performed at a temperature of 15° to 50° C. and a pH of 5 to 9.

By the phrase "cultivating aerobic biomass which utilizes nicotinic acid or its salts", the following is meant: if biomass is cultivated, for example, from sewage sludge as an inoculum with the described molar nicotinic acid-mineral salt ratio under aerobic conditions, an aerobic biomass which utilizes nicotinic acid is obtained, i.e., a biomass that grows with nicotinic acid as sole (only) carbon, nitrogen and energy source in the presence of oxygen. As inoculum soil, samples from various countries can also be used, such as, soil from the city park in Stanander (Spain) or soil from the vineyard in Visperterminen near Visp (Switzerland).

The process is performed not with homogeneous (biologically pure) cultures of microorganisms, but it is performed with a biomass consisting of mixed cultures.

The molar ratio of nicotinic acid to the mineral acid, i.e., the addition of the mixture consisting of nicotinic acid and mineral acid to the cell suspension, takes place so that during the entire cultivation phase a molar ratio of nicotinic acid to mineral acid of 1 to 8 is assured. As mineral acids, for example, sulfuric acid, hydrochloric acid, nitric acid or phosphoric acid can be used, preferably sulfuric acid is used. Suitably the addition of the mixture takes place during the cultivation of the biomass [step (a)] so that a molar ratio of nicotinic acid to sulfuric acid of 3 to 5 is assured. That is, suitably 3 to 5 mol of nicotinic acid per mol of sulfuric acid is used for the cultivation. Preferably 4 to 5 mol of nicotinic acid per mol of sulfuric acid is used for the cultivation.

Usually the cultivation of the aerobic biomass which utilizes nicotinic acid, takes place in a mineral salt medium, preferably in the mineral salt medium whose composition is described in Table 1 below. The cultivation of the biomass takes place suitably at a pH of 5 to 9, preferably at pH 6 to 8. Suitably the temperature during the cultivation of the biomass is between 15° and 50° C., preferably between 25° and 40° C. Usually the cultivation of the biomass takes place over a period of 0.5 to 3 days.

Suitably, under these conditions microorganisms of species *Pseudomonas acidovorans* DSM 7205, or species *Pseudomonas acidovorans* DSM 7203, or species *Alcaligenes faecalis* DSM 7204 or microorganisms with the designation DSM 7202, or their mixtures, are concentrated in the cultivation phase.

The microorganisms DSM 7205, DSM 7203, DSM 7204 and DSM 7202 were deposited on Aug. 13, 1992 in the Deutsche Sammlung von Mikroorganismen und Zellkulturen GmbH [German Collection for Microorganisms and Cell Cultures GmbH], Mascheroderweg 1b, D-3300 Braunschweig, Germany, according to the Budapest Treaty. These microorganisms are not yet known from the literature and accordingly are also a component of the invention. It was not yet possible to identify the microorganism with the designation DSM 7202 taxonomically nor to assign it to a genus.

The taxonomy of microorganisms *Pseudomonas acidovorans* DSM 7205, *Pseudomonas acidovorans* DSM 7203, and *Alcaligenes faecalis* DSM 7204 is described below.

Taxonomic description of *Pseudomonas acidovorans* DSM 7205 is:

| Properties of the strain: | |
| --- | --- |
| cell shape | rods |
| width, micron | 0.8–0.9 |
| length, micron | 1.5–9.0 |
| mobility | + |
| flagella | polar 1 |
| gram reaction | − |
| lysis by 3% KOH | + |
| aminopeptidase (Cerny) | + |
| spores | − |
| oxidase | + |
| catalase | + |
| growth | |
| anaerobic | − |
| 37°/41° C. | +/− |
| pH 5.7 | − |
| MacConkey's broth | + |
| SS agar | + |
| Cetrimide agar | + |
| testosterone | − |
| pigments | |
| nondiffusing | − |
| diffusing | − |
| fluorescent | − |
| pyocyanine | − |
| acid from (OF test) | |
| aerobic glucose | ? |
| anaerobic glucose | − |
| alkaline glucose | + |
| gas from glucose | − |
| acid from | |
| glucose | − |
| fructose | + |
| xylose | − |
| adonite | − |
| L-arabinose | − |
| cellobiose | − |
| dulcitol | − |
| glycerol | + |
| m-inositol | − |
| lactose | − |
| maltose | − |
| raffinose | − |
| L-rhamnose | − |

-continued

| Properties of the strain: | |
|---|---|
| salicin | − |
| D-sorbitol | − |
| saccharose | − |
| trehalose | − |
| ethanol | + |
| dulcitol | − |
| ONPG/PNPG | − |
| ADH | − |
| VP | − |
| indole | − |
| NO$_2$ from NO$_3$ | + |
| phenylalanine desaminase | w |
| levan from saccharose | − |
| lecithinase | − |
| urease | − |
| hydrolysis of | |
| starch | − |
| gelatin | − |
| casein | w |
| DNA | − |
| Tween 80 | + |
| aesculin | − |
| PHB | − |
| tyrosine catabolism | + |
| use of substrate | |
| acetate | + |
| adipate | + |
| caprate | + |
| citrate | + |
| glycolate | + |
| laevulinate | + |
| malate | + |
| malonate | + |
| phenyl acetate | + |
| L-arabinose | − |
| fructose | + |
| glucose | − |
| mannose | − |
| maltose | − |
| D-xylose | − |
| mannitol | + |
| gluconate | + |
| 2-ketogluconate | + |
| N-acetylglucosamine | − |
| L-serine | − |
| quinate | + |
| D,L-tryptophan | + |
| L-tartrate | + |
| acetamide | + |
| α-aminobutyrate | + |
| ethanol | w |

Taxonomic description of *Pesudomonas acidovorans* DSM 7203 is:

| Properties of the strain: | |
|---|---|
| cell shape | rods |
| width, micron | 0.8–1.0 |
| length, micron | 2.6–6.0 |
| mobility | + |
| flagella | polar 1 |
| gram reaction | − |
| lysis by 3% KOH | + |
| aminopeptidase (Cerny) | + |
| spores | − |
| oxidase | + |
| catalase | + |
| growth | |
| anaerobic | − |
| 37°/41° C. | +/− |
| pH 5.7 | − |
| MacConkey's broth | + |
| SS agar | + |
| Cetrimide agar | + |
| testosterone | − |
| pigments | |
| nondiffusing | − |

-continued

| Properties of the strain: | |
|---|---|
| diffusing | − |
| fluorescent | − |
| pyocyanine | − |
| acid from (OF test) | |
| aerobic glucose | ? |
| anaerobic glucose | − |
| alkaline glucose | + |
| gas from glucose | − |
| acid from | |
| glucose | − |
| fructose | + |
| xylose | − |
| adonite | − |
| L-arabinose | − |
| cellobiose | − |
| dulcitol | − |
| glycerol | + |
| m-inositol | + |
| lactose | − |
| maltose | − |
| raffinose | − |
| L-rhamnose | − |
| salicin | − |
| D-sorbitol | − |
| saccharose | − |
| trehalose | − |
| ethanol | −? |
| dulcitol | − |
| ONPG/PNPG | − |
| ADH | − |
| VP | − |
| indole | − |
| NO$_2$ from NO$_3$ | + |
| phenylalanine desaminase | w |
| levan from saccharose | − |
| lecithinase | − |
| urease | − |
| hydrolysis of | |
| starch | − |
| gelatin | − |
| casein | + |
| DNA | − |
| Tween 80 | + |
| aesculin | − |
| PHB | − |
| tyrosine catabolism | + |
| use of substrate | |
| acetate | + |
| adipate | + |
| caprate | + |
| citrate | + |
| glycolate | + |
| laevulinate | + |
| malate | + |
| malonate | + |
| phenyl acetate | + |
| L-arabinose | − |
| fructose | + |
| glucose | − |
| mannose | − |
| maltose | − |
| D-xylose | − |
| mannitol | + |
| gluconate | + |
| 2-ketogluconate | + |
| N-acetylglucosamine | − |
| L-serine | − |
| quinate | + |
| D,L-tryptophan | + |
| L-tartrate | + |
| acetamide | + |
| α-aminobutyrate | w |
| ethanol | + |

Taxonomic description *Alcaligenes faecalis* DSM 7204 is:

| Properties of the strain: | |
|---|---|
| cell shape | rods |
| width, micron | 0.6–0.8 |
| length, micron | 1.0–2.0 |
| mobility | + |
| flagella | peritrichous |
| gram reaction | − |
| lysis by 3% KOH | + |
| aminopeptidase (Cerny) | + |
| oxidase | + |
| catalase | + |
| growth | |
| anaerobic | − |
| 37°/41° C. | +/+ |
| pH 5.7 | − |
| MacConkey's broth | + |
| SS agar | + |
| Cetrimide agar | + |
| pigments | |
| nondiffusing | − |
| diffusing | − |
| fluorescent | − |
| pyocyanine | − |
| acid from (OF test) | |
| aerobic glucose | ? |
| anaerobic glucose | − |
| alkaline glucose | + |
| gas from glucose | − |
| acid from | |
| D-glucose | − |
| D-fructose | + |
| D-xylose | − |
| ONPG/PNPG | − |
| ADH | − |
| VP | − |
| indole | − |
| $NO_2$ from $NO_3$ | + |
| dentrification | − |
| phenylalanine desaminase | − |
| levan from saccharose | − |
| lecithinase | − |
| urease | − |
| hydrolysis of | |
| starch | − |
| gelatin | − |
| casein | − |
| DNA | − |
| Tween 80 | − |
| aesculin | − |
| tyrosine catabolism | + |
| use of substrate | |
| acetate | + |
| adipate | − |
| caprate | + |
| citrate | + |
| glycolate | + |
| laevulinate | − |
| D-malate | + |
| malonate | + |
| phenyl acetate | + |
| L-arabinose | − |
| D-fructose | − |
| D-glucose | − |
| D-mannose | − |
| maltose | − |
| D-xylose | − |
| mannitol | − |
| gluconate | − |
| 2-ketogluconate | + |
| N-acetylglucosamine | − |
| L-serine | − |

Herein, the phrase "heterocyclic carboxylic acid (substrate) to be hydroxylated" is meant to also include its salts, such as, its water soluble alkaline salts.

After the cultivation, the biomass can then be separated for the actual biotransformation (hydroxylation) either in a way usual to one skilled in the art or the heterocyclic carboxylic acid (general formula VIII) to be hydroxylated is directly added to the cultivated biomass.

The actual hydroxylation of the heterocyclic carboxylic acid (substrate) takes place in a way known to one skilled in the art with nongrowing cells. Preferably the actual hydroxylation of the heterocyclic carboxylic acid takes place with the microorganisms concentrated in the cultivation phase of the species Pseudomonas acidovorans DSM 7205, species Pseudomonas acidovorans DSM 7203, species Alcaligenes faecalis DSM 7204 or microorganisms with the designation DSM 7202, or with mixtures of these.

As the substrate, for example, nicotinic acid, pyrazine carboxylic acid or their halogenated derivatives can be used. As the halogenated derivatives of nicotinic acid or pyrazine carboxylic acid, for example, 5-chloronicotinic acid, 4-chloronicotinic acid or 6-chloropyrazine carboxylic acid can be used. Preferably nicotinic acid is hydroxylated to 6-hydroxynicotinic acid or pyrazine carboxylic acid is hydroxylated to 5-hydroxypyrazine carboxylic acid. The substrate for the biotransformation can be added continuously or batchwise. Suitably the substrate addition takes place so that the substrate amount in the fermenter does not exceed 20 percent by weight, preferably 15 percent by weight.

As medium for the hydroxylation those usual to one skilled in art can be used, preferably either the mineral salt medium described in Table 1 or the A-N medium described in Table 4. Usually the biotransformation is performed with cells that have an optical density at 550 nm ($OD_{550}$) or at 650 nm ($OD_{650}$) of 5 to 100. Suitably the biotransformation is performed at a pH of 5 to 9, preferably of 6.5 to 7.5 and at a suitable temperature of 15° to 50° C., preferably of 25° to 35° C.

After a usual reaction time of 5 to 24 hours the hydroxylated heterocyclic carboxylic acid, according to general formula VII, can be isolated by methods usual to one skilled in the art, e.g., by acidification of the cell-free fermentation solution or by precipitation in the form of poorly soluble salts. Preferably as the hydroxylated heterocyclic carboxylic acid, 6-hydroxynicotinic acid or 5-hydroxypyrazine carboxylic acid is isolated.

EXAMPLE A (a) Cultivation of the Biomass

The fermentation was performed in an unsterile mineral salt medium (Table 1) with 1 g of nicotinic acid per liter, in a fermenter with a working volume of 15 l at pH 7.0, at a temperature of 30° C. and an aeration rate between 5 to 20 l/min. For pH regulation, only acid in the form of an aqueous suspension consisting of 307 g of nicotinic acid (2.5 mol) and 49 g (0.5 mol) of $H_2SO_4$ and 1 l water from a vessel with a stirrer, which was fastened to the cover of the fermenter by a pneumatically controlled ball valve, was added to the medium. The fermenter was inoculated with 500 ml of sewage sludge from the waste water purification plant, Visp, Switzerland (Table 2). After 36 hours the fermenter was emptied except for one liter and filled with fresh medium. This procedure was repeated after another 24 hours, 48 hours and 72 hours.

(b) Hydroxylation (production of 6-Hydroxynicotinic Acid)

When the optical density at 550 nm had reached a value between 5 to 20, the biomass was used to spectrophotometrically measure the specific 6-hydroxynicotinic acid formation rate. For this purpose, first the biomass was washed once with 0.9 percent (w/v) of NaCl solution. Then 10 μl of this cell suspension was added to a quartz cuvette (1 cm light path) preheated to 30° C., that contained 2990 μl of a solution consisting of 6.5 g of nicotinic acid/l, 10.1 g of $K_2HPO_4$/l and 4.0 g of $KH_2PO_4$/l, pH 7.0. The absorption of the cuvette at 550 nm was measured and then, from the same vessel, the linear increase of the absorption at 295 nm per minute was calculated. The specific activity (U) was determined according to the formula below:

$$U = \frac{A_{295nm} \cdot 60}{OD_{550nm} \cdot \min}$$

The fermentations were repeated with a sludge sample from the Zermatt (Switzerland) sewage treatment plant, soil samples from Visperterminen, Switzerland, and soil samples from Lac de Joux, Switzerland and a soil sample from Santander, Spain (Table 2).

TABLE 1

Composition of the mineral salt medium

TABLE 1-continued

| | |
|---|---|
| $MgCl_2.6H_2O$ | 0.8 g/l |
| $CaCl_2$ | 0.16 g/l |
| $Na_2SO_4$ | 0.25 g/l |
| $K_3PO_4.2H_2O$ | 0.7 g/l |
| $Na_3PO_4.12H_2O$ | 2.4 g/l |
| SLF | 1.0 ml/l |
| FeEDTA | 15.0 ml/l |
| Composition of the trace elements (SLF) in the mineral salt medium: | |
| KOH | 15.0 g/l |
| $EDTANa_2.2H_2O$ | 100.0 g/l |
| $ZnSO_4.7H_2O$ | 9.0 g/l |
| $MnCl_2.4H_2O$ | 4.0 g/l |
| $H_3BO_3$ | 2.7 g/l |
| $CoCl_2.6H_2O$ | 1.8 g/l |
| $CuCl_2.2H_2O$ | 1.5 g/l |
| $NiCl_2.6H_2O$ | 0.18 g/l |
| $Na_2MoO_4.2H_2O$ | 0.2 g/l |
| Composition of FeEDTA: | |
| EDTA $Na_2.2H_2O$ | 5.0 g/l |
| $FeSO_4.7H_2O$ | 2.0 g/l |
| (The pH of the solution was adjusted to 7.0) | |

TABLE 2

| Inoculum | $OD_{550}$ before activity measurement | Special activity $(A_{295} \cdot OD_{550}^{-1})$ | |
|---|---|---|---|
| (1) ARA LONZA | 5.3 | 35.5 | |
| (2) Lac de Joux | 14 | 20 | |
| (3) ARA Zermatt | 9.6 | 26 | |
| (4) Vineyard V'terminen | 12 | 44 | |
| (5) soil Spain | 10 | 32 | |
| (6) control | 3.5 | 35.1 | } double determination |
| Pseudomonas acidovorans | 8 | 39 | |

Note:
Places where the microorganisms were found:
(1) Sewage sludge from the sewage treatment plant of the LONZA company in Visp, Switzerland.
(2) Soil from the banks of Lac de Joux, Le Sentier, Switzerland.
(3) Sewage sludge from the sewage treatment plant in Zermatt, Switzerland.
(4) Soil from the vineyard in Visperterminen in Visp, Switzerland.
(5) Soil from the city park in Santander, Spain

EXAMPLE B

Production of 5-Hydroxypyrazine Carboxylic Acid

The biomass from fermentations 4, 5 and 6 (Table 2) were centrifuged off and washed once in 0.9 percent (w/v) NaCl solution. Then the cells were resuspended in a liter of solution containing 0.5 mol (70 g) of pyrazine carboxylic acid ammonia salt, pH 7.0. The optical density at 650 nm was then 20. After an incubation time of 16 hours under aerobic conditions at pH 7.0 and a temperature of 30° C., a quantitative conversion from pyrazine carboxylic acid to 5-hydroxypyrazine carboxylic acid could be determined by UV spectroscopy. The formed 5-hydroxypyrazine carboxylic acid was not catabolized from the microorganisms.

As a control test Pseudomonas acidovorans D3 (DSM 4746), which is especially suitable for the industrial production of 5-hydroxypyrazine carboxylic acid cultured as was described above, was used for the reaction according to the process described in European Patent Application 92110425.3. The results are summarized in Table 2.

EXAMPLES C TO F

From the cultivated biomass according to Example A (a), the following microorganisms were able to be concentrated:
Pseudomonas acidovorans DSM 7205
Pseudomonas acidovorans DSM 7203
Alcaligenes faecalis DSM 7204
microorganisms with the designation DSM 7202.

These microorganisms were cultivated under the following conditions and used for the hydroxylation of nicotinic acid from 6-hydroxynicotinic acid. The results are summarized in Table 3.

In this connection the microorganisms were cultivated in a 7 l fermenter containing 5 l of A-N medium (Table 4) with 2 g of sodium nicotinate per l at a temperature of 30° C. and a pH of 7.0. For pH regulation, 5N NaOH and 8.5 percent (v/v) $H_3PO_4$ were used. After 18 hours of growth, an additional 2 g of sodium nicotinate per l was added to the fermentation solution. As soon as the cells were in the exponential growth phase, the fermentation was interrupted and the microorganisms separated from the medium by centrifugation. Then the cells were resuspended in 500 ml of a solution containing 0.27 mol (40 g) of sodium nicotinate, pH 7.0. The optical density was then 20. The hydroxylation of nicotinic acid to 6-hydroxynicotinic acid was tracked spectrophotometrically (Table 3).

TABLE 3

| Examples | Time necessary for the hydroxylation of 0.27 mol nicotinic acid in 500 ml | Isolated amount of 6-hydroxynicotinic acid after acidification of the cell-free solution | Yield in % relative to nicotinic acid |
| --- | --- | --- | --- |
| Example 3: DSM 7202 | 22 hours | 15.7 g (0.11 mol) | 41 |
| Example 4: DSM 7203 | 9 hours | 30.1 g (0.22 mol) | 80 |
| Example 5: DSM 7204 | 10 hours | 28.1 g (0.2 mol) | 73 |
| Example 6: DSM 7205 | 5 hours | 32.0 g (0.23 mol) | 85 |

TABLE 4

| A + N medium | |
| --- | --- |
| Composition | Concentration (mg/l) |
| Na$_2$HPO$_4$ | 2000 |
| KH$_2$PO$_4$ | 1000 |
| NaCl | 3000 |
| MgCl$_2$.6H$_2$O | 400 |
| CaCl$_2$.2H$_2$O | 14.5 |
| FeCl$_3$.6H$_2$O | 0.8 |
| pyridoxal hydrochloride | $10 \cdot 10^{-3}$ |
| riboflavin | $5 \cdot 10^{-3}$ |
| nicotinic acid amide | $5 \cdot 10^{-3}$ |
| thiamine hydrochloride | $2 \cdot 10^{-3}$ |
| biotin | $2 \cdot 10^{-3}$ |
| pantothenic acid | $5 \cdot 10^{-3}$ |
| p-aminobenzoate | $5 \cdot 10^{-3}$ |
| folic acid | $2 \cdot 10^{-3}$ |
| vitamin B12 | $5 \cdot 10^{-3}$ |
| ZnSO$_4$.7H$_2$O | $100 \cdot 10^{-3}$ |
| MnCl$_2$.4H$_2$O | $90 \cdot 10^{-3}$ |
| H$_3$BO$_3$ | $300 \cdot 10^{-3}$ |
| CoCl$_2$.6H$_2$O | $200 \cdot 10^{-3}$ |
| CuCl$_2$.2H$_2$O | $10 \cdot 10^{-3}$ |
| NiCl$_2$.6H$_2$O | $20 \cdot 10^{-3}$ |
| Na$_2$MoO$_4$.2H$_2$O | $30 \cdot 10^{-3}$ |
| EDTANa$_2$.2H$_2$O | $5 \cdot 10^{-3}$ |
| FeSO$_4$.7H$_2$O | $2 \cdot 10^{-3}$ |
| (pH of the solution was adjusted to 7.0) | |

What is claimed is:

1. A process for the production of a carboxylic acid chloride of an aromatic nitrogen heterocycle of a series of compounds of formulas:

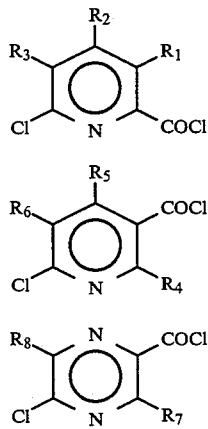

wherein R$_1$, R$_2$, R$_3$, R$_4$, R$_5$, R$_6$, R$_7$ and R$_8$ are the same or different and each is a hydrogen atom or a halogen atom, comprising chlorinating, respectively, a hydroxy carboxylic acid of an aromatic nitrogen heterocycle of a series of compounds of formulas:

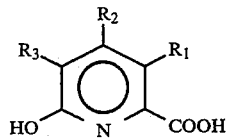

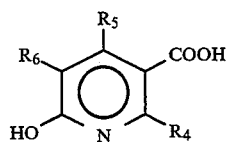

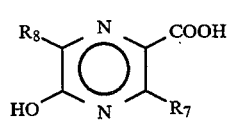

wherein R$_1$ to R$_8$ have the above-mentioned meanings, the chlorination being performed with a solution of phosphorous pentachloride in phosphoroxy chloride, converting the excess phosphorous pentachloride into phosphoroxy chloride either with a C$_1$-C$_4$-carboxylic acid or with a silane of formula:

$$(CH_3)_3-Si-OR_9 \quad\quad VII$$

wherein R$_9$ is a C$_1$-C$_4$-alkyl group or a tri(C$_1$-C$_4$)alkylsilyl group, and then isolating the product according to one of the formulas I to III.

2. The process according to claim 1 wherein formic acid is used as the C$_1$-C$_4$-carboxylic acid.

3. The process according to claim 1 wherein methoxytrimethyl silane, wherein R$_9$ is a methyl group, or hexamethyl disiloxane, wherein R$_9$ is a trimethyl group, is used as the silane of the formula VII.

4. The process according to claim 3 wherein, as the hydroxy carboxylic acid of the aromatic nitrogen heterocycle of the formula IV, 6-hydroxypicolinic acid, wherein R$_1$, R$_2$ and R$_3$ is a hydrogen atom, or 6-hydroxy-3,5-dichloropicolinic acid, wherein R$_2$ is a hydrogen atom and R$_1$ and R$_3$ each is a chloride atom, or, as the hydroxy carboxylic acid of the aromatic nitrogen heterocycle of the formula VI, 5-hydroxypyrazine carboxylic acid, wherein R$_7$ and R$_8$ each is a hydrogen atom, is used.

5. The process according to claim 4 wherein the chlorination is performed at a temperature of 20° to 110° C.

6. The process according to claim 5 wherein the addition of the C$_1$-C$_4$-carboxylic acid or the silane of the formula VII is performed at a temperature of 0° to 60° C.

7. The process according to claim 6 wherein the phosphoroxy chloride is removed by distillation.

8. The process according to claim 1 wherein the chlorination is performed at a temperature of 20° to 110° C.

9. The process according to claim 1 wherein the addition of the C$_1$-C$_4$-carboxylic acid or the silane of the formula VII is performed at a temperature of 0° to 60° C.

10. The process according to claim 1 wherein the phosphoroxy chloride is removed by distillation.

11. 3,5,6-Trichloro-picolinic acid chloride, which is the compound of the formula I, wherein R$_1$ and R$_3$ is each a chlorine atom and R$_2$ is a hydrogen atom.

* * * * *

UNITED STATES PATENT AND TRADEMARK OFFICE
CERTIFICATE OF CORRECTION

PATENT NO. : 5,364,939
DATED : Nov. 15, 1994
INVENTOR(S) : Roduit

It is certified that error appears in the above-identified patent and that said Letters Patent is hereby corrected as shown below:

On the Title Page, insert the following information:

[73] Assignee: Lonza Ltd., Gampel/Valais, Switzerland

Signed and Sealed this

Twenty-first Day of March, 1995

Attest:

BRUCE LEHMAN

Attesting Officer      Commissioner of Patents and Trademarks